(12) United States Patent
Follstad (10) Patent No.: US 7,645,609 B2
(45) Date of Patent: Jan. 12, 2010

(54) METHOD FOR CONTROLLING SIALYLATION OF PROTEINS PRODUCED BY MAMMALIAN CELLS

(75) Inventor: Brian D. Follstad, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 215 days.

(21) Appl. No.: 10/620,064

(22) Filed: Jul. 15, 2003

(65) Prior Publication Data
US 2004/0115768 A1 Jun. 17, 2004

Related U.S. Application Data

(60) Provisional application No. 60/396,221, filed on Jul. 15, 2002.

(51) Int. Cl.
C12N 5/00 (2006.01)
(52) U.S. Cl. ................ 435/358; 435/325; 435/383; 435/391; 435/392; 435/404; 435/405
(58) Field of Classification Search .............. 435/325, 435/358, 383, 391, 392, 404, 405
See application file for complete search history.

(56) References Cited

U.S. PATENT DOCUMENTS

| | | | |
|---|---|---|---|
| 5,047,335 A | 9/1991 | Paulson et al. | |
| 5,443,968 A | 8/1995 | Takazawa et al. | |
| 5,672,502 A | 9/1997 | Birch et al. | |
| 5,858,783 A * | 1/1999 | Goodwin et al. | ............ 435/373 |
| 6,204,012 B1 | 3/2001 | Hellmuth et al. | |
| 6,274,568 B1 | 8/2001 | Schnaar et al. | |
| 6,472,175 B1 | 10/2002 | Wood | |
| 6,673,575 B1 | 1/2004 | Franze et al. | |
| 2002/0142386 A1 | 10/2002 | Betenbaugh et al. | |
| 2004/0214228 A9 | 10/2004 | Venkataraman et al. | |

FOREIGN PATENT DOCUMENTS

| | | |
|---|---|---|
| AU | 744086 | 2/2002 |
| CA | 2 351 637 | 5/2000 |
| JP | 4-281797 | 7/1992 |
| JP | 6-292592 | 10/1994 |

OTHER PUBLICATIONS

Bauer CH et al., "Alterations of D-galactose metabolism in Morris hepatomas," Cancer Res 1980; 40:2026-2032.
Brown E et al., "Biochemical expression of the galactosemic defect in lymphocytes and the effects on glycoprotein synthesis," Metabolism 1977; 26(9)1047-1055.
Gu X, "Characterization and improvement of interferon-γ glycosylation in Chinese hamster ovary cell culture," Thesis, Massachusetts Institute of Technology, Dept. of Chemical Eng., Oct. 26, 2001.
Gu X and Wang DIC, "Sialylation of interferon-γ in Chinese hamster ovary cell culture," Abstracts of Papers American Chemical Society, 1997; 213(1-3):BIOT 106.
Gu X and Wang DIC, "Improvement of interferon-γ sialylation in Chinese hamster ovary cell culture by feeding of N-acetylmannosamine," Biotechnol Bioeng 1998; 58:642-648.
Hughes RC et al., "Effect of 2-deoxy- D -glucose on the cell-surface glycoproteins of hamster fibroblasts," Eur J Biochem 1977; 72:265-273.
Panneerselvam K et al., "Human fibroblasts prefer mannose over glucose as a source of mannose for N-Glycosylation," J Biol Chem 1997; 272(37):23123-23129.
Schumacher U et al., "Is the lectin binding pattern of human breast and colon cancer cells influenced by modulators of sialic acid metabolism?" Histochem Cell Biol 1996; 106:599-604.
Thomas GH et al., "Accumulation of N-acetylneuraminic acid (sialic acid) in human fibroblasts cultured in the presence of N-acetylmannosamine," Biochim Biophys Acta 1985; 846:37-43.
Wasley LC et al., "The importance of N- and O-linked oligosaccharides for the biosynthesis and in vitro and in vivo biologic activities of erythropoietin," Blood 1991; 77(12):2624-2632.
Kaufmann, H. et al., "Comparative analysis of two controlled proliferation strategies regarding product quality, influence on tetracycline-regulated gene expression, and productivity," Biotechnology And Bioengineering 72(6):592-602, 2001.
Kawaguchi, T. et al., "A new approach to the modification of cell membrane glycosphingolipids: ganglioside composition of JTC-12 P3 cells altered by feeding with galactose as a sole carbohydrate source in protein-free and lipid-free synthetic medium," Exp. Cell Res. 179(2):507-516, 1988.
Keppler, O. et al., "UDP-GlcNAc 2-Epimerase: A regulator of cell surface sialylation," Sci. 284:1372-1376, 1999.
Miller-Podraza, H. et al., "Biosynthesis and localization of gangliosides in cultured cells," Biochem. 21(14):3260-3265, 1982.
Stephanopoulos, G. and Vallino, J., "Network rigidity and metabolic engineering in metabolite overproduction," Science 252:1675-1681, 1991.
Vriezen, N. and van Dijken, J., "Fluxes and enzyme activities in central metabolism of myeloma cells grown in chemostat culture," Biotech. & Bioeng. 59(1):28-39, 1998.
Wang, D., "Engineering of CHO cell glycosylation through CMP-Sialic acid transporter over expression," Biochemical Engineering XIV, Session VI—Physiology of Protein Expression, Engineering Conferences International, Harrison Hot Springs, BC, Canada, Jul. 10-14, 2005.
Yoon Sung Kwan et al., "Effect of low culture temperature on specific productivity and transcription level of anti-4-1BB antibody in recombinant Chinese hamster ovary cells," Biotech. Progress 19(4):1383-1386, 2003.
Zanghi, J. et al., "Role of nucleotide sugar pools in the inhibition of NCAM polysialylation by ammonia," Biotech. Progress 14(6):834-844, 1998.

(Continued)

Primary Examiner—L Blaine Lankford
(74) Attorney, Agent, or Firm—Rosemary Sweeney (57) ABSTRACT

The invention provides media and methods for culturing mammalian cells whereby the sialylation of a protein produced by the cells is increased. The medium can contain N-acetylmannosamine and, optionally, galactose. The medium may also comprise fructose and mannose. Alternatively, the medium can contain galactose and fructose and, optionally, can also comprise mannose and/or N-acetylmannosamine. The methods can be practiced along with other methods for culturing cells so as to increase the quantity or quality of a protein produced by the cells, including culturing the cells at a temperature below 37° C.

28 Claims, 3 Drawing Sheets

OTHER PUBLICATIONS

Duval, D. et al., "Role of metabolic waste products in the control of cell proliferation and antibody production by mouse hybridoma cells," *Hybridoma* 11(3):311-322, 1992.

Grossman, S.I. and Turner, J.E., *In*: Mathematics for the Biological Sciences, Macmillan Publishing Co., Inc., New York, NY, pp. 24-30, 1974.

Jayme, D.W., "Nutrient optimization for high density biological production applications," *Cytotechnol* 15-30, 1991.

Jenkins, N. et al., "Getting the glycosylation right: implications for the biotechnology industry," *Nature Biotechnol* 14:975-981, 1996.

Panneerselvam, K. et al., "Human fibroblasts prefer mannose over glucose as a source of mannose for N-glycosylation," *J Biol Chem* 272(37):23123-23129, 1997.

Panneerselvam, K. and Freeze, H.H., "Mannose corrects altered N-glycosylation in carbohydrate-deficient glycoprotein syndrome fibroblasts," *J. Clin. Invest.* 97(6):1478-1487, 1996.

Panneerselvam, K. et al., "Abnormal metabolism of mannose in families with carbohydrate-deficient glycoprotein syndrome type 1," *Biochem. and Mol. Med.* 61:161-167, 1997.

Rearick, J.I., "Glucose starvation alters lipid-linked oligosaccharide biosynthesis in chinese hamster ovary cells," *J Biol. Chem.* 256(12):6255-6261, 1981.

Stark, N.J. et al., "Glucose-dependent glycosylation of secretory glycoprotein in mouse myeloma cells," *Arch. Biochem. Biophys.* 192(2):599-609, 1979.

Tachibana, H. et al., "Changes of monosaccharide availability of human hybridoma lead to alteration of biological properties of human monoclonal antibody," *Cytotechnology* 16:151-157, 1994.

Wasley, L.C. et al., "The importance of N- and O-linked oligosaccharides for the biosynthesis and in vitro and in vivo biologic activities of erythropoietin," *Blood* 77(12):2624-2632, 1991.

Altamirano, J. J. et al, "Decoupling cell growth and product formation in Chinese hamster ovary cells through metabolic control," *Biotechnol Bioeng* 76:351-360, 2001.

Coroadinha, A. S. et al., "Effect of medium sugar source on the production of retroviral vectors for gene therapy," *Biotechnol Bioeng* 94(1):24-36, 2006.

Stryer, L., Biochemistry $2^{nd}$ Edition, W. H. Freeman and Company, San Francisco, 1981, p. 104.

Chun et al., "Application of factorial design to accelerate identification of CHO growth factor requirements," *Biotechnol. Prog.* 19:52-57, 2003.

Mantey et al., "Efficient biochemical engineering of cellular sialic acids using an unphysiological sialic acid precursor in cells lacking UDP-N-acetylglucosamine 2-epimerase," *FEBS Lett.* 503:80-84, 2001.

Proprietor's Observations, Main Request and Auxiliary Request, submitted Mar. 28, 2007 in response to Notices of Opposition filed in European Patent No. 1 036 179 (in German with English translation).

Baker, K. N. et al., "Metabolic control of recombinant protein N-glycan processing in NSO and CHO cells," *Biotecnhol Bioeng* 73:188-202, 2001.

Ghannoum, M. A. et al., "In vitro determination of optimal antifungal combinations against *Cryptococcus neoformans* and *Candida albicans*," *Antimicrob Agents Chemother* 39(11):2459-2465, 1995.

Hills, A. E. et al., "Metabolic control of recombinant monoclonal antibody N-glycosylation in GS-NSO cells," *Biotechnol Bioeng* 75:239-251, 2001.

Kadoya, Toshihiko, Experiment Report, document D12 of European Opposition EP 1 036 179; Sep. 28, 2004 (translation).

Nyberg, G. B. et al., "Metabolic effects on recombinant interferon-γ glycosylation in continuous culture of Chinese hamster ovary cells," *Biotechnol Bioeng* 62(3):336-347, 1999.

Nyberg, G. B., "Glycosylation site occupancy heterogeneity in Chinese hamster ovary cell culture," Ph.D. Thesis, Massachusetts Institute of Technology, 1998.

* cited by examiner

METHOD FOR CONTROLLING SIALYLATION OF PROTEINS PRODUCED BY MAMMALIAN CELLS

This application claims benefit of U.S. Provisional Application No. 60/396,221, filed Jul. 15, 2002, which is incorporated herein in its entirety.

FIELD OF THE INVENTION

The invention relates to methods and media for controlling the sialylation of a protein produced by cultured cells.

BACKGROUND

Proteins are useful in a variety of diagnostic, pharmacologic, agricultural, nutritional, and research applications. Given the high cost of producing proteins, especially therapeutic proteins, even small increases in the efficiency of production or in the function and stability of a protein can be valuable. The function and stability, and hence the utility, of a protein can be affected by the posttranslational addition of sugar residues to the protein to form a glycoprotein. For example, the addition of terminal sialic acid residues to polysaccharides attached to a glycoprotein generally increases the protein's lifetime in the bloodstream and can, in particular cases, also affect solubility, thermal stability, resistance to protease attack, antigenicity, and specific activity of some glycoproteins. See e.g. Gu and Wang (1998), Biotechnol. and Bioeng. 58(6): 642-48; Morell et al. (1968), J. Biol. Chem. 243(1): 155-59. It is therefore desirable to increase the sialic acid content of a glycoprotein, especially a glycoprotein to be used for pharmacologic applications.

SUMMARY

The invention provides media and methods for culturing mammalian cells so as to produce a protein, optionally a secreted recombinant protein, and to control or, optionally, to increase, the sialic acid content of the protein. The invention provides a method for increasing production and/or sialylation of a protein by mammalian cells comprising culturing the cells in a medium comprising galactose and fructose. The medium may be serum free and may also comprise N-acetylmannosamine and/or mannose. The concentrations of galactose, mannose, and fructose can each be from about 0.1 mM to about 40 mM, from about 0.5 mM to about 20 mM, from about 1 mM to about 10 mM, or from about 1 mM to about 5 mM. The concentration of N-acetylmannosamine can be at least about 0.8 mM, optionally at least about 2 mM, 3 mM, 4 mM, 5 mM, 10 mM, or 20 mM. The protein can be a secreted, recombinant protein, and the mammalian cells can be CHO cells. The cells may be cultured at a temperature from about 29° C. to about 35° C.

In another embodiment, the invention provides a medium, optionally a serum free medium, for culturing mammalian cells comprising galactose and fructose and, optionally, N-acetylmannosamine and/or mannose. Galactose, mannose, and fructose can be a concentrations from about 0.1 mM to about 40 mM each, from about 0.5 mM to about 20 mM each, from about 1 mM to about 10 mM each, or from about 1 mM to about 5 mM each. N-acetylmannosamine can be at a concentration of at least about 0.8 mM, 1 mM, 5 mM, 10 mM, 15 mM, or 20 mM.

In one embodiment, the invention encompasses a method for controlling the sialic acid content of a protein comprising culturing a mammalian cell that produces the protein in medium comprising N-acetylmannosamine and galactose. The medium can further comprise fructose and mannose. Optionally, fructose and mannose can each be present at a concentration from about 1.5 mM to about 4.5 mM. Fructose and mannose can be at the same or different concentrations. The cell can be cultured at a temperature from about 29° C. to about 37° C., optionally, at a temperature from about 29° C. to about 36° C., or from about about 30° C. to about 35° C. The concentration of N-acetylmannosamine in the medium can be at least about 0.8 mM, and the concentration of galactose in the medium can be from about 1.5 mM to about 4.5 mM. The protein can be a secreted protein and/or a recombinant protein and can be produced in a CHO cell.

In a further embodiment, the invention comprises a combination with a medium for culturing mammalian cells in which galactose and N-acetylmannosamine and, optionally, also fructose and mannose are combined with the medium. Fructose can be at a concentration from about 1.5 mM to about 4.5 mM, and mannose can be at a concentration from about 1.5 mM to about 4.5 mM. N-acetylmannosamine can be at a concentration of at least about 0.8 mM, and galactose can be at a concentration from about 1.5 mM to about 4.5 mM. The mammalian cells can be CHO cells, and the medium can be serum-free.

Further, the invention provides an improved method for producing a protein by culturing mammalian cells that express the protein comprising culturing the mammalian cells at a temperature from about 29° C. to about 35° C. in a medium comprising N-acetylmannosamine. The medium can also comprise galactose and, optionally, also fructose and mannose. The concentration of galactose, mannose and fructose can be from about 1.5 mM to about 4.5 mM each. The concentrations of galactose, mannose and fructose can be the same as or different from each other. The concentration of N-acetylmannosamine can be at least about 0.8 mM, and the medium can be serum-free. The mammalian cells can be CHO cells, and the protein can be a secreted, recombinant protein.

Finally, the invention provides a method for controlling the sialic acid content of a recombinant protein comprising culturing mammalian cells that express the recombinant protein at a temperature from about 29° C. to about 35° C. in a medium comprising fructose, galactose, mannose, and N-acetylmannosamine, wherein the concentrations of fructose, galactose, and mannose in the medium are from about 1.5 mM to about 4.5 mM each and wherein the concentration N-acetylmannosamine in the medium is at least 0.8 mM. The concentrations of fructose, mannose, and galactose can be the same as or different from each other.

BRIEF DESCRIPTION OF FIGURES

FIG. 1 shows a net of metabolic pathways leading to sialylation of glycoproteins. Corfield and Schauer (1979), Biol. Cellulaire 35: 213-26; Gu and Wang (1998), Biotechnol. and Bioeng. 58(6): 642-48. Molecules used in the invention are boxed. Negative feedback is shown by a minus sign adjacent to an arrow comprising a dotted line.

DETAILED DESCRIPTION

Definitions

An antibody, as used herein, is a protein or complex of proteins, each of which comprises at least one, or optionally at least two, variable antibody immunoglobulin domains. Antibodies may be single chain antibodies, dimeric antibodies, or some higher order complex of proteins including, but not limited to, heterodimeric antibodies and tetrameric antibodies.

A constant antibody immunoglobulin domain is an immunoglobulin domain that is identical to or substantially similar to a $C_L$, $C_H1$, $C_H2$, $C_H3$, or $C_H4$, domain of human or animal origin. See e.g. Hasemann and Capra, Immunoglobulins: Structure and Function, in William E. Paul, ed., Fundamental Immunology, Second Edition, 209, 210-218 (1989). An antibody immunoglobulin domain is at least 10 amino acids in length, optionally, at least 15, 20 25, 30, 35, 40, 50, 60, 70, 80, or 90 amino acids in length.

An $F_c$ portion of an antibody includes human or animal immunoglobulin domains $C_H2$ and $C_H3$ or immunoglobulin domains substantially similar to these. For discussion, see Hasemann and Capra, supra, at 212-213.

A glycoprotein, as used herein, is a protein that has been modified by the addition of one or more carbohydrates, including, especially, the addition of one or more sugar residues.

An oligosaccharide or polysaccharide is a chain of two or more sugar residues linked by covalent chemical bonds.

Sialylation, as used herein, is the addition of a sialic acid residue to a protein, which may be a glycoprotein.

The term sialic acid, as used herein, encompasses a family of sugars containing 9 or more carbon atoms, including a carboxyl group. A generic structure encompassing all known natural forms of sialic acid is shown below.

R1 groups at various positions on a single molecule can be the same as or different from each other. R1 can be a hydrogen or an acetyl, lactyl, methyl, sulfate, phosphate, anhydro, sialic acid, fucose, glucose, or galactose group. R2 can be an N-acetyl, N-glycolyl, amino, hydroxyl, N-glycolyl-O-acetyl, or N-glycolyl-O-methyl group. R3 represents the preceding sugar residue in an oligosaccharide to which sialic acid is attached in the context of a glycoprotein. R3 can be galactose (connected at its 3, 4, or 5 position), N-acetyl-galactose (connected at its 6 position), N-acetyl-glucose (connected at its 4 or 6 position), sialic acid (connected at its 8 or 9 position), or 5-N-glycolyl-neuraminic acid. Essentials of Glycobiology, Ch. 15, Varki et al., eds., Cold Spring Harbor Laboratory Press, New York (1999). More than 40 forms of sialic acid have been found in nature. Essentials of Glycobiology, Ch. 15, Varki et al., eds., Cold Spring Harbor Laboratory Press, New York (1999). A common form of sialic acid is N-acetyl-neuraminic acid (NANA), in which R1 is a hydrogen at all positions and R2 is an N-acetyl group.

Substantially similar proteins are at least 80%, optionally at least 90%, identical to each other in amino acid sequence and maintain or alter in a desirable manner the biological activity of the unaltered protein. The percent identity of two amino acid or two nucleic acid sequences can be determined by visual inspection and mathematical calculation, or more preferably, the comparison is done by comparing sequence information using a computer program. An exemplary computer program is the Genetics Computer Group (GCG; Madison, Wis.) Wisconsin package version 10.0 program, 'GAP' (Devereux et al. (1984), *Nucl. Acids Res.* 12: 387). The preferred default parameters for the 'GAP' program include: (1) The GCG implementation of a unary comparison matrix (containing a value of 1 for identities and 0 for non-identities) for nucleotides, and the weighted amino acid comparison matrix of Gribskov and Burgess (1986), *Nucl. Acids Res.* 14:6745, as described by Schwartz and Dayhoff, eds., *Atlas of Polypeptide Sequence and Structure*, National Biomedical Research Foundation, pp. 353-358 (1979); or other comparable comparison matrices; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps. The regions of the two proteins that are aligned by GAP for comparison are at least 10 amino acids long, optionally at least 20, 40, 60, 80, 100, 150, 200, 250, or 300 amino acids long. Other programs used by those skilled in the art of sequence comparison can also be used. One of skill in the art will recognize that the parameters chosen can affect the percent identity and will do so more so if the sequences are dissimilar.

A variable antibody immunoglobulin domain is an immunoglobulin domain that is identical or substantially similar to a $V_L$ or a $V_H$ domain of human or animal origin. A variable antibody immunoglobulin domain is at least 10 amino acids in length, optionally, at least 15, 20 25, 30, 35, 40, 50, 60, 70, 80, or 90 amino acids in length.

Description

The addition of carbohydrates to proteins (herein termed the glycosylation of proteins) and the subsequent processing of these carbohydrates can affect the folding, stability, and functional properties of a protein. Lodish et al., Molecular Cell Biology, Chapter 17, W.H. Freeman, New York (2000). For example, the hemagglutinin precursor protein fails to fold properly in the presence of tunicamycin, an antibiotic that interferes with the production of an oligosaccharide precursor necessary for N-linked glycosylation (described below). Id. In addition, a nonglycosylated form fibronectin is secreted normally by fibroblasts, but is degraded more rapidly than glycosylated fibronectin. Lodish et al., supra.

Most secreted proteins and cell surface proteins contain at least one carbohydrate chain; in addition, numerous cytoplasmic and nuclear proteins are also glycosylated. Lodish et al., supra; Essentials of Glycobiology, Ch. 13, Varki et al., eds., Cold Spring Harbor Laboratory Press, New York (1999). A set of enzymes capable of glycosylating proteins is located within the endoplasmic reticulum and the Golgi, organelles that secreted and cell surface proteins pass through on their path to the cell membrane and beyond. The identification of nuclear and/or cytoplasmic enzymes capable of executing similar functions remains uncertain. Essentials of Glycobiology, Ch. 13, Varki et al., eds., Cold Spring Harbor Laboratory Press, New York (1999).

Although protein glycosylation is a complex and variable process, carbohydrate modifications of proteins can be roughly divided into two classes, O-linked glycosylation and N-linked glycosylation. Both of these involve the addition of oligosaccharides to specific amino acids within a protein. O-linked polysaccharides are linked to a hydroxyl group, usually to the hydroxyl group of either a serine or a threonine residue. O-glycans are not added to every serine and threonine residue, and the criteria for determining which serines and threonines will be glycosylated have not been fully elucidated. O-glycans usually comprise one or two branches and comprise from one to four different kinds of sugar residues, which are added one by one. Often, the terminal residue is a sialic acid. In contrast, N-linked polysaccharides are attached to the amide nitrogen of an asparagine. Only asparagines that are part of one of two tripeptide sequences, either asparagine-X-serine or asparagine-X-threonine (where X is any amino acid except proline), are targets for glycosylation. The first step in N-linked glycosylation involves the addition of a complex, pre-formed, branched oligosaccharide consisting of three glucose, nine mannose, and two N-acetylglucosamine residues. This oligosaccharide is further processed by a complex and variable series of steps, resulting in the removal and addition of various sugar residues. In the end product, the terminal residue on each branch of the polysaccharide may be, but is not always, a sialic acid. Lodish et al., supra. N-glycans can have from one to five branches. Varki et al. supra.

Figure 1:
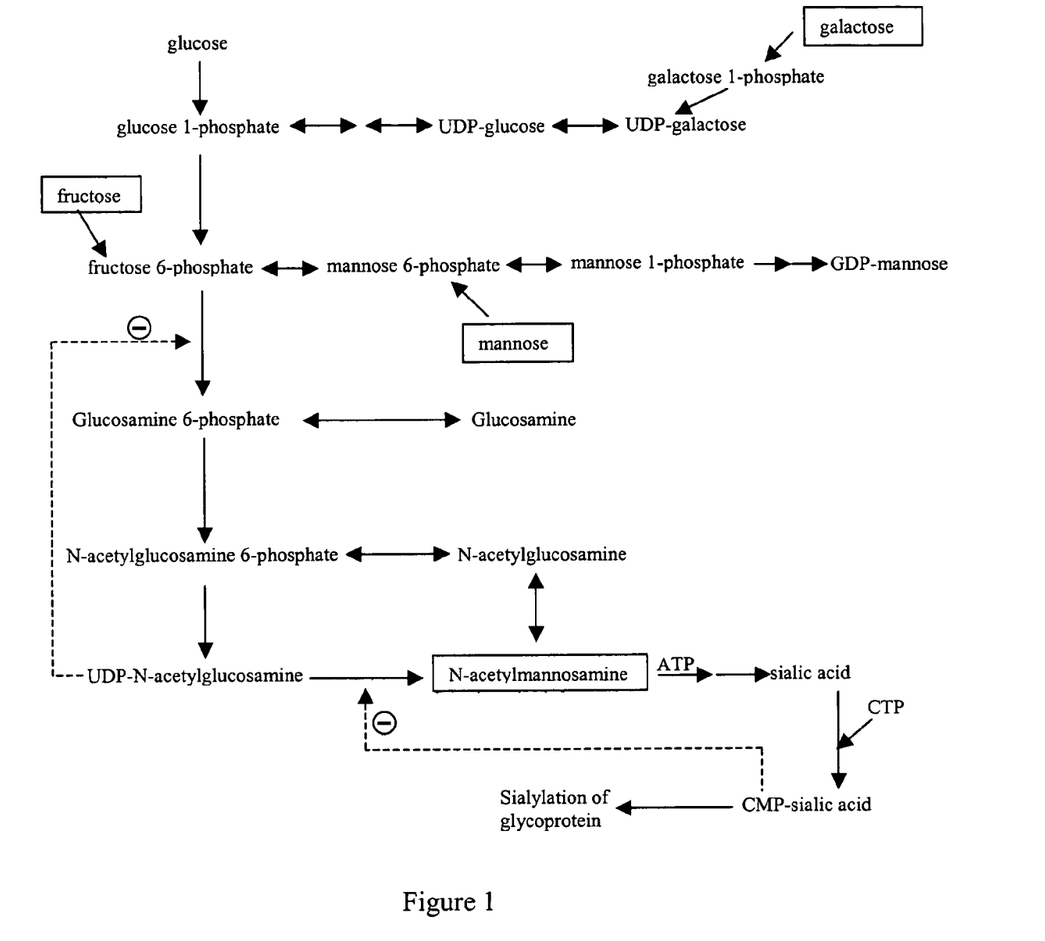

Previous work has elucidated a net of biosynthetic pathways leading to the addition of sialic acid to proteins, as illustrated in FIG. 1. Gu and Wang, supra; Corfield and Schauer, supra. A large variety of molecules are involved at various stages in the synthesis of sialic acid and its attachment to glycoproteins, including sugars such as glucose, mannose, fructose, and galactose, nucleotides such as ATP and CTP, and a host of enzymes needed to catalyze the numerous biosynthetic steps involved, to name just a few of the numerous molecules involved. FIG. 1 also illustrates two points in this net of pathways where negative feedback inhibition is known to occur (dotted lines with arrowheads). Moreover, Gu and Wang (supra) have reported that the addition of N-acetylmannosamine to culture medium results in increased sialylation of a protein produced by the cultured cells. However, the commercial utility of N-acetylmannosamine is currently limited by its expense, and therefore culture conditions or other medium additives with similar or better effects are needed.

Accordingly, the invention provides a method for increasing the sialylation of a glycoprotein produced by a cell culture that comprises adding to the cell culture N-acetylmannosamine and galactose. In a further embodiment, the invention provides a method for increasing the the sialylation of a glycoprotein produced by a cell culture comprising culturing cells in medium comprising N-acetylmannosamine, galactose, fructose, and mannose. Alternatively, sialylation can be increased by culturing the cells in a medium comprising galactose and fructose and, optionally, also N-acetylmannosamine and/or mannose. In still another embodiment, the invention encompasses an improvement of a method for producing a protein comprising culturing mammalian cells that express the protein at a temperature below 37° C., optionally from about 29° C. to about 36° C. or from about 29° C. to about 35° C. or from about 30° C. to about 33° C., in a medium comprising N-acetylmannosamine. In another aspect, the invention provides a culture medium for mammalian cells comprising N-acetylmannosamine, galactose, and, optionally, also fructose and/or mannose. The concentration of N-acetylmannosamine can be at least about 0.8 millimolar (mM), optionally at least about 2 mM, at least about 3 mM, at least about 4 mM, at least about 5 mM, at least about 10 mM, or at least about 20 mM, and the concentration of galactose can be from about 1 mM to about 5 mM, optionally from about 2 mM to about 4 mM, or from about 2.5 mM to about 3.5 mM. The concentrations of fructose and mannose, when present, can be the same as or different from those of each other and those of galactose and N-acetylmannosamine. The concentrations of fructose and mannose can be from about 1 mM to about 5 mM each, optionally from about 2 mM to about 4 mM each, or from about 2.5 mM to about 3.5 mM each.

Alternatively, the invention provides a culture medium for mammalian cells comprising fructose and galactose and, optionally, also mannose and/or N-acetylmannosamine. Fructose, galactose, and mannose can each be present at concentrations from about 0.1 mM each to about 40 mM each, optionally from about 0.5 mM each to about 20 mM each, from about 1.0 mM each to about 10 mM each, or from about 1 mM each to about 5 mM each. Fructose, galactose, and mannose can be present at the same or different concentrations. N-acetylmannosamine can be present at a concentration of at least about 0.8 millimolar (mM), optionally at least about 2 mM, at least about 3 mM, at least about 4 mM, at least about 5 mM, at least about 10 mM, or at least about 20 mM Further, the invention encompasses a culture medium for mammalian cells comprising fructose, galactose, and, optionally, mannose, which can be present at concentrations from about 0.1 mM each to about 40 mM each, optionally from about 0.5 mM each to about 20 mM each, from about 1.0 mM each to about 10 mM each, or from about 1 mM each to about 5 mM each. Fructose, galactose, and mannose can be present at the same or different concentrations.

In one aspect, the invention provides a method for culturing mammalian cells comprising growing in culture a mammalian cell that has been genetically engineered to produce a protein and adding to the culture N-acetylmannosamine, galactose, and, optionally, also fructose and/or mannose. In another aspect, the invention provides a method for culturing a mammalian cell that has been genetically engineered to produce a protein in a medium comprising N-acetylmannosamine at a temperature below 37° C. One kind of genetically engineered cell is a cell that has been transformed with a recombinant vector encoding the protein. The protein can be expressed under the control of a strong viral promoter (e.g. either a cytomegalovirus (CMV) promoter or a simian virus 40 (SV40) promoter) or an inducible promoter (e.g. a metallothionine promoter or a tetracycline-responsive promoter as described in, for example, Gossen and Bujard (1992) Proc. Natl. Acad. Sci. 89: 5547-51). Typically, the cell does not naturally express the protein or expresses the protein only at very low levels (in the absence of genetic engineering).

A protein is generally understood to be a polypeptide of at least 10 amino acids in length, optionally, at least 15, 20, 25, 30, 35, 40, 50, 60, 70, 80, 90, 100, 125, 150, 175, or 200 amino acids in length. The proteins produced using the methods and media of the invention can be secreted proteins.

The methods and media of the invention can be used to increase the sialylation of just about any protein, and is particularly advantageous for polypeptides whose expression is under the control of a strong promoter, such as for example, a viral promoter, and/or polypeptides that are encoded on a message that has an adenoviral tripartite leader element. Examples of useful expression vectors that can be used to produce proteins are disclosed in International Application WO 01/27299 and in McMahan et al., (1991), EMBO J. 10: 2821, which describes the pDC409 vector.

Generally, the methods of the invention are useful for inducing the production of recombinant polypeptides. Proteins that can be produced with the methods and media of the invention include those comprising amino acid sequences identical to or substantially similar to all or part of one of the following proteins: a Flt3 ligand (as described in WO 94/28391), a CD40 ligand (as described in U.S. Pat. No. 6,087,329), erythropoietin, thrombopoietin, calcitonin, leptin, IL-2, angiopoietin-2 (as described by Maisonpierre et al. (1997), Science 277(5322):55-60, incorporated herein by reference), Fas ligand, ligand for receptor activator of NF-kappa B (RANKL, as described in WO 01/36637), tumor necrosis factor (TNF)-related apoptosis-inducing ligand (TRAIL, as described in WO 97/01633), thymic stroma-derived lymphopoietin, granulocyte colony stimulating factor, granulocyte-macrophage colony stimulating factor (GM-CSF, as described in Australian Patent No. 588819), mast cell growth factor, stem cell growth factor (described in e.g. U.S. Pat. No. 6,204,363, incorporated herein by reference), epidermal growth factor, keratinocyte growth factor, megakaryote growth and development factor, RANTES, growth hormone, insulin, insulinotropin, insulin-like growth factors, parathyroid hormone, interferons including α interferons, γ interferon, and consensus interferons (such as those described in U.S. Pat. Nos. 4,695,623 and 4,897,471, both of which are incorporated herein by reference), nerve growth factor, brain-derived neurotrophic factor, synaptotagmin-like proteins (SLP 1-5), neurotrophin-3, glucagon, interleukins 1 through 18, colony stimulating factors, lymphotoxin-β, tumor necrosis factor (TNF), leukemia inhibitory factor, oncostatin-M, and various ligands for cell surface molecules ELK and Hek (such as the ligands for eph-related kinases or LERKS). Descriptions of proteins that can be produced according to the inventive methods may be found in, for example, *Human Cytokines: Handbook for Basic and Clinical Research, Vol. II* (Aggarwal and Gutterman, eds. Blackwell Sciences, Cambridge, Mass., 1998); *Growth Factors: A Practical Approach* (McKay and Leigh, eds., Oxford University Press Inc., New York, 1993); and *The Cytokine Handbook* (A. W. Thompson, ed., Academic Press, San Diego, Calif., 1991), all of which are incorporated herein by reference.

Further proteins that can be produced using the methods and media of the invention include proteins comprising all or part of the amino acid sequence of a receptor for any of the above-mentioned proteins, an antagonist to such a receptor of any of the above-mentioned proteins, and/or or proteins substantially similar to such receptors or antagonists. These receptors and antagonists include: both forms of tumor necrosis factor receptor (TNFR, referred to as p55 and p75, as described in U.S. Pat. No. 5,395,760 and U.S. Pat. No. 5,610, 279), Interleukin-1 (IL-1) receptors (types I and II; described in EP Patent No. 0 460 846, U.S. Pat. No. 4,968,607, and U.S. Pat. No. 5,767,064, all of which are incorporated herein by reference), IL-1 receptor antagonists (such as those described in U.S. Pat. No. 6,337,072, incorporated herein by reference), IL-1 antagonists or inhibitors (such as those described in U.S. Pat. Nos. 5,981,713, 6,096,728, and 5,075,222, all of which are incorporated herein U.S. Pat. No. 5,767,064), by reference), IL-2 receptors, IL-4 receptors (as described in EP Patent No. 0 367 566 and U.S. Pat. No. 5,856,296), IL-15 receptors, IL-17 receptors, IL-18 receptors, granulocyte-macrophage colony stimulating factor receptor, granulocyte colony stimulating factor receptor, receptors for oncostatin-M and leukemia inhibitory factor, receptor activator of NF-kappa B (RANK, described in WO 01/36637 and U.S. Pat. No. 6,271,349), osteoprotegerin (described in e.g. U.S. Pat. No. 6,015,938, incorporated by reference), receptors for TRAIL (including TRAIL receptors 1, 2, 3, and 4), and receptors that comprise death domains, such as Fas or Apoptosis-Inducing Receptor (AIR).

More proteins that can be produced using the methods and media of the invention include proteins comprising all or part of the amino acid sequences of differentiation antigens (referred to as CD proteins) or their ligands or proteins substantially similar to either of these. Such antigens are disclosed in *Leukocyte Typing VI* (*Proceedings of the VIth International Workshop and Conference*, Kishimoto, Kikutani et al., eds., Kobe, Japan, 1996). Similar CD proteins are disclosed in subsequent workshops. Examples of such antigens include CD22, CD27, CD30, CD39, CD40, and ligands thereto (CD27 ligand, CD30 ligand, etc.). Several of the CD antigens are members of the TNF receptor family, which also includes 41BB and OX40. The ligands are often members of the TNF family, as are 41BB ligand and OX40 ligand. Accordingly, members of the TNF and TNFR families can also be produced using the present invention.

Enzymatically active proteins or their ligands can also be produced using the methods and media of the invention. Examples include proteins comprising all or part of one of the following proteins or their ligands or a proteins substantially similar to one of these: metalloproteinase-disintegrin family members, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, ligands for any of the above-mentioned enzymes, and numerous other enzymes and their ligands.

The methods and media of the invention can also be used to produce chimeric proteins selected in vitro to bind to a specific target protein and modify its activity such as those described in International Applications WO 01/83525 and WO 00/24782 and antibodies or portions thereof and chimeric antibodies, i.e. antibodies having human constant antibody immunoglobulin domains coupled to one or more murine variable antibody immunoglobulin domain, fragments thereof, or substantially similar proteins. The method of the invention may also be used to produce conjugates comprising an antibody and a cytotoxic or luminescent substance. Such substances include: maytansine derivatives (such as DM1); enterotoxins (such as a Staphylococcal enterotoxin); iodine isotopes (such as iodine-125); technetium isotopes (such as Tc-99m); cyanine fluorochromes (such as Cy5.5.18); and ribosome-inactivating proteins (such as bouganin, gelonin, or saporin-S6). Examples of antibodies, in vitro-selected chimeric proteins, or antibody/cytotoxin or antibody/luminophore conjugates that can be produced using the methods and media of the invention include those that recognize any one or a combination of proteins including, but not limited to, any of the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-2, IL-3, IL-7, IL-4, IL-5, IL-8, IL-10, IL-2 receptor, IL-4 receptor, IL-6 receptor, IL-13 receptor, IL-18 receptor subunits, PDGF-β and analogs thereof (such as those described in U.S. Pat. Nos. 5,272,064 and 5,149,792), VEGF, TGF, TGF-β2, TGF-β1, EGF receptor (including those described in U.S. Pat. No. 6,235,883 B1) VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002), Cytokine Growth Factor Rev. 13(1):19-25), C5 complement, IgE, tumor antigen CA125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, L-selectin, IFN-γ, Respiratory Syncitial Virus, human immunodeficiency virus (HIV), hepatitis B virus (HBV), *Streptococcus mutans*, and *Staphylococcus aureus*.

The methods and media of the invention can also be used to produce all or part of a protein that is an anti-idiotypic antibody or a substantially similar protein, including anti-idiotypic antibodies against: an antibody targeted to the tumor antigen gp72; an antibody against the ganglioside GD3; an antibody against the ganglioside GD2; or antibodies substantially similar to these.

The methods and media of the invention can also be used to produce recombinant fusion proteins comprising any of the above-mentioned proteins or substantially similar proteins. For example, recombinant fusion proteins comprising one of the above-mentioned proteins plus a multimerization domain, such as a leucine zipper, a coiled coil, an Fc portion of an antibody, or a substantially similar protein, can be produced using the methods and media of the invention. See e.g. WO 94/10308; Lovejoy et al. (1993), Science 259: 1288-1293; Harbury et al. (1993), Science 262: 1401-05; Harbury et al. (1994), Nature 371:80-83; Hakansson et al. (1999), Structure 7: 255-64. Specifically included among such recombinant fusion proteins are proteins in which at least a portion of TNFR or RANK is fused to an Fc portion of an antibody (TNFR:Fc or RANK:Fc). TNFR:Fc comprises the Fc portion of an antibody fused to an extracellular domain of TNFR, which includes amino acid sequences substantially similar to amino acids 1-163, 1-185, or 1-235 of FIG. 2A of U.S. Pat. No. 5,395,760. RANK:Fc is described in WO 01/36637.

Suitable cells for practicing the present invention include any cell line that can glycosylate proteins, preferably a mammalian cell line that has been genetically engineered to express a protein, although the invention can also be used to produce non-recombinant proteins. Preferably, the cells are homogenous cell lines. Numerous suitable cell lines are known in the art. For example, Chinese hamster ovary (CHO), HeLa, VERO, BHK, Cos, MDCK, 293, 3T3, myeloma (e.g. NSO, NSI), or WI38 cells may be used. Hybridoma cell lines that produce an antibody can also be used to practice the invention. Cell lines derived from the above-mentioned cells are also suitable for practicing the invention.

Particularly preferred cells are CHO cells, which are widely used for the production of recombinant proteins, e.g. cytokines, clotting factors, and antibodies (Brasel et al. (1996), Blood 88: 2004-2012; Kaufman et al. (1988), J. Biol Chem 263:6352-6362; McKinnon et al. (1991), J Mol Endocrinol 6: 231-239; Wood et al. (1990), J. Immunol 145: 3011-3016). A dihydrofolate reductase (DHFR)-deficient mutant cell line (Urlaub et al. (1980), Proc. Natl. Acad. Sci. USA 77:4216-4220), such as DXB11 or DG-44, is useful because the efficient DHFR selectable and amplifiable gene expression system allows high level recombinant protein expression in these cells (Kaufman (1990), Meth. Enzymol. 185: 527-566). In addition, these cells are easy to manipulate as adherent or suspension cultures and exhibit relatively good genetic stability. CHO cells and recombinant proteins expressed in them have been extensively characterized and have been approved for use in clinical commercial manufacturing by regulatory agencies.

According to the present invention, a mammalian host cell is cultured under conditions that promote the production of the protein of interest, which can be an antibody or a recombinant protein. Basal cell culture medium formulations for culturing mammalian cells are well known in the art. See e.g. Freshney, Culture of Animal Cells: A Manual of Basic Technique, p. 69-84, Wiley-Liss (1987). To these basal culture medium formulations the skilled artisan will add components such as amino acids, salts, sugars, vitamins, hormones, growth factors, buffers, antibiotics, lipids, trace elements and the like, depending on the requirements of the host cells to be cultured. The skilled artisan may also choose to use one of the many individualized media formulations that have been developed to maximize cell growth, cell viability, and/or recombinant protein production in a particular cultured cell. The methods according to the current invention may be used in combination with commercially available cell culture media or with a cell culture medium that has been individually formulated for use with a particular cell line. The culture medium may or may not contain serum and/or protein. Suitable commercial media include RPMI 1641 Medium, Dulbecco's Modified Eagle's Medium, Minimal Essential Medium Eagle, F-12K and F12 Medium, McCoy's 5A Medium, Leibovitz's L-15 Medium, and serum-free media such as EX-CELL™ 300 Series (available from JRH Biosciences, Lenexa, Kans., USA), among others, which can be obtained from the American Type Culture Collection or JRH Biosciences, as well as other vendors.

The skilled artisan may also choose to use one of the many individualized media formulations that have been developed to maximize cell growth, cell viability, and/or recombinant polypeptide production in a particular cultured host cell. The methods according to the current invention may be used in combination with commercially available cell culture media or with a cell culture medium that has been individually formulated for use with a particular cell line. For example, an enriched medium that could support increased polypeptide production may comprise a mixture of two or more commercial media, such as, for instance, DMEM and Ham's F12 media combined in ratios such as, for example, 1:1, 1:2, 1:3, 1:4, 1:5, 1:6, 1:7, 1:8, or even up to 1:15 or higher. Alternatively or in addition, a medium can be enriched by the addition of nutrients, such as amino acids or peptone, and/or a medium (or most of its components with the exceptions noted below) can be used at greater than its usual, recommended concentration, for example at 2×, 3×, 4×, 5×, 6×, 7×, 8×, or even higher concentrations. As used herein, "1×" means the standard concentration, "2×" means twice the standard concentration, etc. In any of these embodiments, medium components that can substantially affect osmolarity, such as salts, cannot be increased in concentration so that the osmolarity of the medium falls outside of an acceptable range. Thus, a medium may, for example, be 8× with respect to all components except salts, which can be present at only 1×. An enriched medium may be serum free and/or protein free. In this context, "protein free" means free of proteins of at least 15 amino acids, such as insulin or insulin-like growth factor. "Protein free" medium can contain hydrolyzed proteins, such as are found in peptones (from yeast, soy, or other sources), which are commonly used medium additives. Further, a medium may be supplemented periodically during the time a culture is maintained to replenish medium components that can become depleted such as, for example, vitamins, amino acids, and metabolic precursors. As is known in the art, different media and temperatures may have somewhat different effects on different cell lines, and the same medium and temperature may not be suitable for all cell lines.

The methods of the invention are useful for inducing the production of recombinant proteins. Recombinant proteins are proteins produced by the process of genetic engineering. The term "genetic engineering" refers to infecting, transfecting, transforming, or transducing a cell with a recombinant polynucleotide molecule so as to cause the cell to alter expression of a desired protein. In some embodiments, such a recombinant polynucleotide molecule comprises nucleic acids encoding the protein of interest operably linked to suitable regulatory sequences, which are part of an "expression vector" into which the nucleic acids encoding the protein of interest are inserted.

Methods and vectors for genetically engineering cells and/or cell lines to express a protein of interest are well known to those skilled in the art; for example, various techniques are illustrated in *Current Protocols in Molecular Biology*, Ausubel et al., eds. (Wiley & Sons, New York, 1988, and quarterly updates); Sambrook et al., *Molecular Cloning: A Laboratory Manual* (Cold Spring Laboratory Press, 1989); and Kaufman, R. J., *Large Scale Mammalian Cell Culture*, 1990, pp. 15-69. Additional protocols using commercially available reagents, such as the cationic lipid reagents LIPOFECTAMINE™, LIPOFECTAMINE™-2000, or LIPOFECTAMINE™-PLUS (which can be purchased from Invitrogen), can be used to transfect cells. Felgner et al. (1987), *Proc. Natl. Acad. Sci. USA* 84: 7413-7417. In addition, electroporation or bombardment with microprojectiles coated with nucleic acids can be used to transfect cells using procedures, such as those in Sambrook et al. (1989), *Molecular Cloning: A Laboratory Manual*, 2nd ed. Vol. 1-3, Cold Spring Harbor Laboratory Press, and Fitzpatrick-McElligott (1992), Biotechnology (NY) 10(9):1036-40. Genetic engineering techniques include, but are not limited to, transformation of cells with expression vectors, targeted homologous recombination and gene activation (see e.g. U.S. Pat. No. 5,272,071 to Chappel), and trans activation by engineered transcription factors (see e.g. Segal et al. (1999), Proc. Natl. Acad. Sci. USA 96(6): 2758-63).

A gene encoding a selectable marker is often used to facilitate the identification of recombinant cells and is therefore often included in expression vectors. Selection of transformants can be performed using methods such as, for example, the dihydrofolate reductase (DHFR) selection scheme or resistance to cytotoxic drugs. Kaufman et al. (1990), Meth. in Enzymology 185: 487-511). A suitable host strain for DHFR selection can be, for example, CHO strain DX-B11, which is deficient in DHFR. Urlaub and Chasin (1980), *Proc. Natl. Acad. Sci. USA* 77: 4216-4220. Other examples of selectable markers include those conferring resistance to antibiotics, such as G418 and hygromycin B.

The regulatory sequences are typically derived from mammalian, microbial, viral, and/or insect genes. Examples of regulatory sequences include transcriptional promoters, operators, and enhancers, ribosome binding sites (see e.g. Kozak (1991), J. Biol. Chem. 266: 19867-19870), sequences that can control transcriptional and translational termination, polyadenylation signals (see e.g. McLauchlan et al. (1988), Nucleic Acids Res. 16: 5323-33), and matrix and scaffold attachment sites (see Phi-Van et al. (1988), Mol. Cell. Biol. 10: 2302-07; Stief et al. (1989), Nature 341:342-35; Bonifer et al. (1990), EMBO J. 9: 2843-38). Nucleotide sequences are operably linked when the regulatory sequence functionally relates to the protein coding sequence. Such sequences can be present in cis or in trans as long as they functionally relate to the protein-coding sequence. Thus, a promoter nucleotide sequence is operably linked to a protein coding sequence if the promoter nucleotide sequence controls the transcription of the coding sequence. Although many sequences capable of regulating expression, such as promoters, exert their effects when present in cis, this need not always be the case. For example, non-coding RNAs present in trans may downregulate or enhance gene expression. See e.g. Storz (2002), Science 296:1260-63.

Commonly used promoter and enhancer sequences are derived from polyoma virus, adenovirus 2, simian virus 40 (SV40), and human cytomegalovirus (CMV). For example, the human CMV promoter/enhancer of immediate early gene 1 may be used. See e.g. Patterson et al. (1994), Applied Microbiol. Biotechnol. 40: 691-98. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., Nature 273:113, 1978; Kaufman (1990), Meth. in Enzymol. 185: 487-511). Smaller or larger SV40 fragments can also be used, provided the approximately 250 bp sequence extending from the Hind III site toward the Bgl I site located in the SV40 viral origin of replication site is included.

A sequence encoding an appropriate native or heterologous signal peptide (leader sequence) can be incorporated into an expression vector, to promote extracellular secretion of the recombinant protein. The choice of signal peptide or leader depends on the type of host cells in which the recombinant protein is to be produced. Examples of signal peptides that are functional in mammalian host cells include the signal sequence for interleukin-7 (IL-7) described in U.S. Pat. No. 4,965,195, the signal sequence for interleukin-2 receptor described in Cosman et al., Nature 312:768, 1984; the interleukin-4 receptor signal peptide described in EP Patent No. 367,566; the type I interleukin-1 receptor signal peptide described in U.S. Pat. No. 4,968,607; and the type II interleukin-1 receptor signal peptide described in EP Patent No. 460,846.

Additional control sequences shown to improve expression of heterologous genes from mammalian expression vectors include such elements as the expression augmenting sequence element (EASE) derived from CHO cells (Morris et al., in *Animal Cell Technology*, pp. 529-534 (1997); U.S. Pat. No. 6,312,951 B1; U.S. Pat. No. 6,027,915; U.S. Pat. No. 6,309,841 B1) and the tripartite leader (TPL) and VA gene RNAs from Adenovirus 2 (Gingeras et al. (1982), *J. Biol.*

Chem. 257:13475-13491). Internal ribosome entry site (IRES) sequences of viral origin allow dicistronic mRNAs to be translated efficiently (Oh and Sarnow (1993), *Current Opinion in Genetics and Development* 3: 295-300; Ramesh et al. (1996), *Nucleic Acids Research* 24:2697-2700). Expression of a heterologous cDNA as part of a dicistronic mRNA followed by the gene for a selectable marker (e.g. DHFR) has been shown to improve transfectability of the host and expression of the heterologous cDNA (Kaufman et al. (1990), *Methods in Enzymol.* 185: 487-511). Exemplary expression vectors that employ dicistronic mRNAs are pTR-DC/GFP described by Mosser et al., *Biotechniques* 22:150-161 (1997), and p2A5I described by Morris et al., in *Animal Cell Technology*, pp. 529-534 (1997).

Examples of useful expression vectors that can be used to produce proteins are those disclosed in WO 01/27299 and the pDC409 vector described in McMahan et al. (1991), *EMBO J.* 10: 2821. Another useful high expression vector, pCAVNOT, has been described by Mosley et al. (1989), *Cell* 59: 335-348. Other expression vectors for use in mammalian host cells can be constructed as disclosed by Okayama and Berg (*Mol. Cell. Biol.* 3: 280 (1983)). A useful system for stable high level expression of mammalian cDNAs in C127 murine mammary epithelial cells can be constructed substantially as described by Cosman et al. (*Mol. Immunol.* 23: 935 (1986)). A useful high expression vector, PMLSV N1/N4, described by Cosman et al. (1984), *Nature* 312: 768, has been deposited as ATCC 39890. Additional useful mammalian expression vectors are described in EP Patent No. A 0 367 566 and WO 01/27299. The vectors can be derived from retroviruses. In place of the native signal sequence, a heterologous signal sequence can be added, such as the signal sequence for IL-7 described in U.S. Pat. No. 4,965,195; the signal sequence for IL-2 receptor described in Cosman et al. (*Nature* 312: 768 (1984)); the IL-4 signal peptide described in EP Patent No. 367,566; the type I IL-1 receptor signal peptide described in U.S. Pat. No. 4,968,607; and the type II IL-1 receptor signal peptide described in EP Patent No. 460,846.

Suitable culture conditions and for mammalian cells are known in the art. See e.g. Animal cell culture: A Practical Approach, D. Rickwood, ed., Oxford University Press, New York (1992). Mammalian cells may be cultured in suspension or while attached to a solid substrate. Furthermore, mammalian cells may be cultured, for example, in fluidized bed bioreactors, hollow fiber bioreactors, packed bed bioreactors, fibrous bed bioreactors, roller bottles, shake flasks, or stirred tank bioreactors, with or without microcarriers, and operated in a batch, fed batch, continuous, semi-continuous, or perfusion mode.

The methods and media of the invention can be combined with other methods or medium additives, especially those that increase production or sialylation of a protein. For example, cells can be grown at temperatures from about 29° C. to about 40° C., optionally from about 29° C. to about 37° C., from about 29° C. to about 36° C., from about 29° C. to about 35° C., or from about 30° C. to about 33° C. Moreover, substances other than N-acetylmannosamine, galactose, fructose, and mannose can be added to the medium. Such substances include, but are not limited to, histone deacetylase inhibitors, butyrate, trichostatin, caffeine, and hexamethylene bisacetamide.

The methods according to the present invention may be used to increase the titer and/or sialylation of proteins in both single phase and multiple phase culture processes. In a single phase process, cells are inoculated into a culture environment and the disclosed methods and media are employed during the single production phase. In a multiple stage process, cells are cultured in two or more distinct phases. For example cells may be cultured first in a growth phase, under environmental conditions that maximize cell proliferation and viability, then transferred to a production phase, under conditions that increase production and/or sialylation of a protein. In multiple phase processes the methods and media according to the present invention are employed at least during the production phase.

The examples presented below are not intended to be exhaustive or to limit the scope of the invention. The skilled artisan will understand that modifications and variations are possible in light of the above teachings, and such modifications and variations are intended to be within the scope of the invention. All references cited herein, both supra and infra, are incorporated herein in their entirety.

EXAMPLE 1

Comparison of the Ability of Various Sugars and Combinations Thereof to Induce Sialylation of TNFR:$F_c$ The following experiment was done to determine which carbohydrate or combination of carbohydrates added to cell culture medium is able to induce the most sialylation of TNFR:Fc produced by the cells. The relative extent of sialylation was determined by measuring the fraction of TNFR:Fc produced by a cell culture that elutes from an anion exchange column only at a high salt concentration. This provides a rough measure of the extent of sialylation because proteins with more sialic acid require a higher salt concentration for elution from an anion exchange column.

Figure 2:
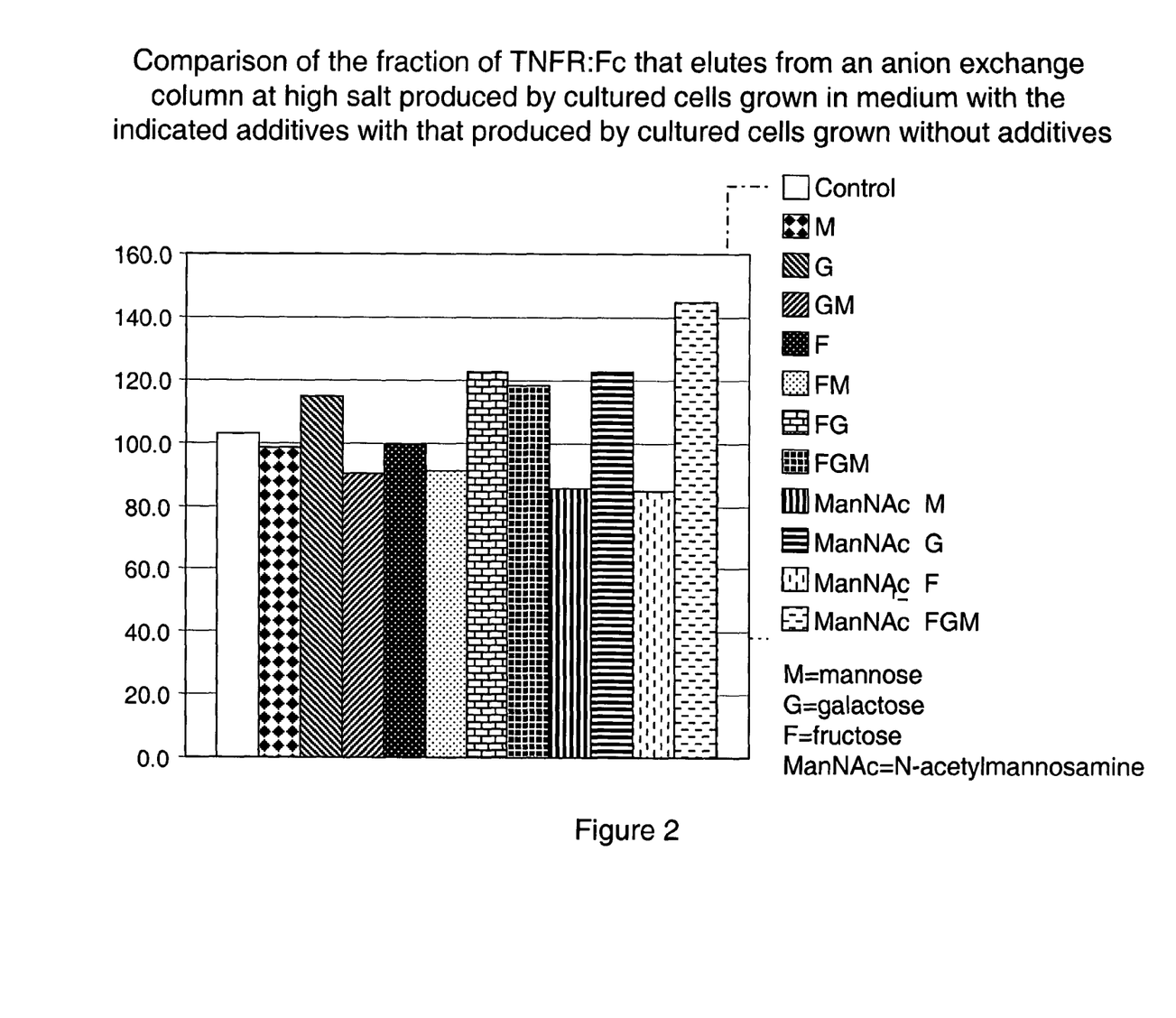
FIG. 2 compares the high salt-eluting fraction of the extracellular region of tumor necrosis factor receptor fused to the Fc region of an antibody (TNFR:Fc, which is described in U.S. Pat. No. 5,395,760) on an anion exchange column when TNFR:Fc is produced by cultures grown in media with the indicated additives. All samples, including that produced by a culture without additives (labeled "Control"), are compared to a single batch of TNFR:Fc produced in a separate experiment by cultures grown without medium additives.

About $2.0 \times 10^6$ cells of a CHO cell line that had been genetically engineered to produce TNFR:Fc were inoculated into each of 12 flasks containing 30 ml of serum-free medium with INTRALIPIDS™ (a sterile emulsion of fractionated soybean oil and fractionated egg phospholipids in water), insulin-like growth factor-I, and butyrate and without any added carbohydrates (labeled "control") or with the carbohydrate additives indicated in FIG. 2 at a concentration of 4 mM each. Cultures were incubated for 7 days at 30° C. with shaking at 150 revolutions per minute. TNFR:Fc was harvested from the medium after seven days of growth and pre-purified by Protein A affinity chromatography. Thereafter, the purified TNFR:Fc protein concentration was determined by measuring absorbance at 280 nanometers. The concentration of the TNFR:Fc protein was adjusted to about 0.25 mg/ml by dilution into 20 mM imidazole, pH 6.2.

An anion exchange column (4.6 mm in diameter and 50 mm high) was run as follows. The column was calibrated both before and after running experimental samples using a mixture of two control proteins containing 0.25 mg/ml soybean trypsin inhibitor and 0.5 mg/ml lactalbumin (both obtained from Sigma-Aldrich Corporation, St. Louis, Mo., USA). A sample of up to 200 µl of this mixture was applied to the column, and a linear gradient between 20 mM imidazole, pH 6.2 (Buffer A) and 20 mM imidazole, 0.7 M NaCl, pH 6.2 (Buffer B) was run through the column at a rate of 0.8 ml/min. At 22.1 minutes, the gradient was complete, and the column contained 100% Buffer B. Elution of protein was determined by monitoring absorbance at 280 nanometers, and a graph of these measurements versus time (relative to the time of loading) was recorded automatically as the protein eluted from the column. Lactalbumin eluted before soybean trypsin inhibitor (about 11.2 minutes as compared to 15.4 minutes). Between runs, the column was cleaned by injecting 0.2 ml 2M NaCl, followed by two sets of alternating washes with Buffers A and B followed by a final wash with Buffer A.

A volume of up to 200 µl (at about 0.25 mg/ml) of TNFR: Fc was loaded onto the anion exchange column, and a linear gradient was run through the column as explained above. The portion of the TNFR:Fc peak that eluted after soybean trypsin inhibitor was considered to elute at high salt. The fraction of TNFR:Fc that eluted at high salt was determined by comparing the area under the curve that eluted after soybean trypsin inhibitor with the total area under the curve. This number was compared in each case with a similar fraction from a batch of TNFR:Fc produced in a separate experiment by a cell culture grown without mannose, fructose, galactose, or N-acetylmannosamine.

The results are shown in FIG. 2. The fact that the control culture from the present experiment without added sugars is only very slightly above 100% indicates that the sialylation of TNFR:Fc can be almost constant from batch to batch. These data also indicate that cultures grown in N-acetylmannosamine, fructose, mannose, and galactose (at concentrations of 4 mM each) produced the highest levels of sialylation of TNFR:Fc of any of the combinations tested. Further, TNFR:Fc from cultures grown with the following combinations of sugars also showed increases in sialylation: (1) galactose alone; (2) fructose and galactose; (3) fructose, galactose, and mannose; and (4) N-acetylmannosamine and galactose.

EXAMPLE 2

Sampling of a Response to Determine Optimal Concentrations of N-Acetylmannosamine and Sugars This experiment was done to determine optimal concentrations for N-acetylmannosamine and fructose, mannose, and galactose in growth medium for increasing sialylation of TNFR:Fc. The experiment also seeks to determine a combination that achieves the most sialylation of TNFR:Fc with the lowest concentration of N-acetylmannosamine.

Figure 3:
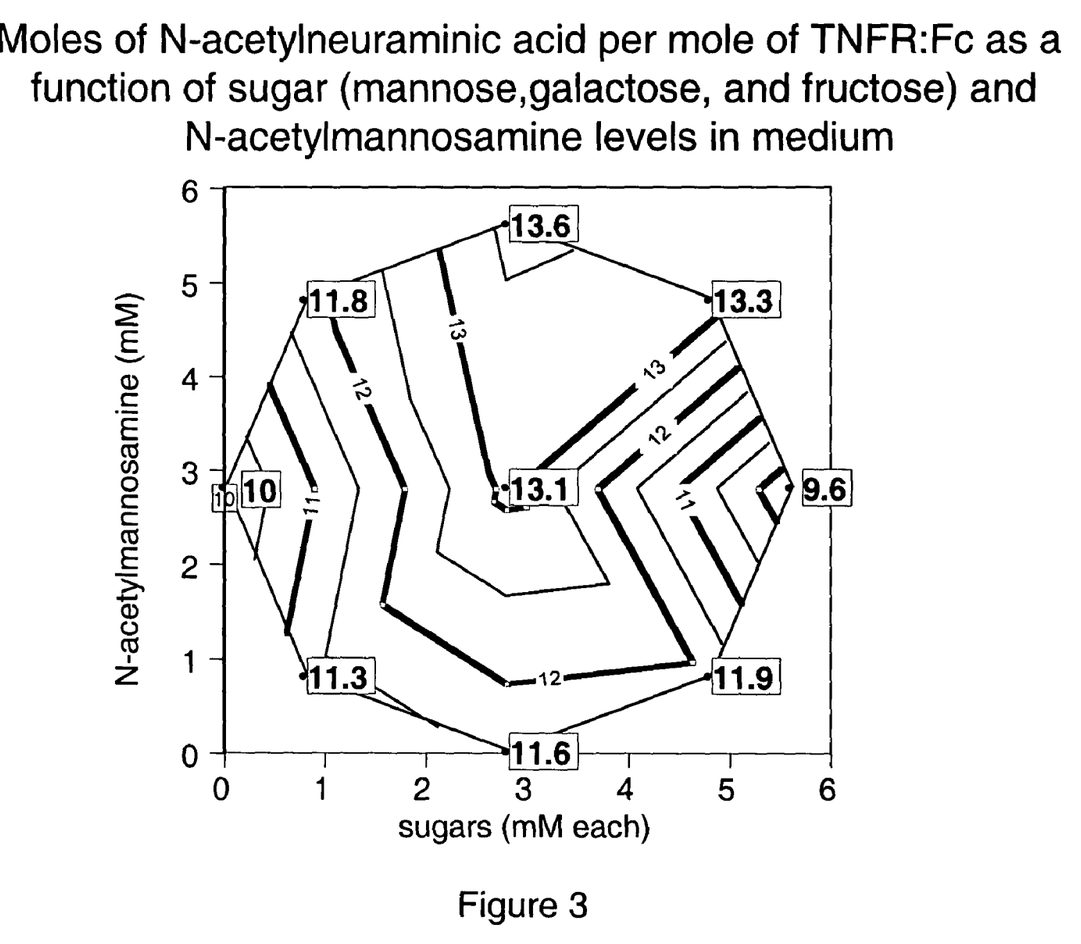
FIG. 3 is a contour plot made using the JMP computer software (described below) showing the moles of N-acetyl-neuraminic acid (NANA) per mole of TNFR:Fc (printed in bold and boxed next to each data point sampled in this experiment and labeled as part of each contour line) produced by cultured cells grown in media with the indicated concentrations of N-acetylmannosamine and sugars (fructose, galactose, and mannose).

About $2.0\times10^6$ cells of the same CHO cell line used in Example 1 were inoculated into each of 13 flasks containing 30 ml of serum-free medium with INTRALIPIDS™ (a sterile emulsion of fractionated soybean oil and fractionated egg phospholipids in water), insulin-like growth factor-I, and butyrate with the medium additives indicated in FIG. 3, that is, varying concentrations of N-acetylmannosamine and/or a sugar cocktail containing equimolar amounts of fructose, galactose, and mannose.

Combinations of concentrations of medium additives were chosen to sample a response surface. See e.g. Öberg and Deming, Chemical Eng. Process, April, 2000: 53-59. Five duplicate cultures were used to produce the data for the center point of FIG. 3, and eight other cultures each produced the data for one of the eight axial points of FIG. 3. TNFR:Fc was harvested from the medium after 7 days of growth at 30° C. with shaking at 150 revolutions per minute and pre-purified by Protein A affinity chromatography. The number of moles of N-acetylneuraminic acid (NANA) per mole of recombinant protein was determined as follows. Following Protein A affinity chromatography, the concentration of TNFR:Fc was determined by reading absorbance at 280 nanometers, and protein concentration was adjusted to 1 mg/ml by dilution into phosphate buffered saline. Sialidase (obtained from Glyko, Inc. of Novato, Calif., USA) was diluted to 1 mU/µl (where 1 unit is the amount of enzyme necessary to cleave 1 µmole of NANA per minute at pH 5 and 37° C.) in 2× Incubation Buffer (200 mM sodium acetate, pH 5.0). TNFR:Fc and sialidase (10 µl each) were mixed and incubated for 4 hours at 37° C. Thereafter, the mixture was diluted to 0.2 mg/ml of TNFR:Fc by adding 30 µl of water. The sialic acid released was detected and quantitated using high performance anion exchange chromatography, in which the outflow was monitored using pulsed amperometric detection. Pulsed amperometric detection utilizes electrodes that intersperse cleaning pulses (to remove analytes that foul the electrode and prevent accurate readings) with detection pulses at a potential appropriate to detect NANA. The system was calibrated both before and after running experimental samples using known amounts of NANA purchased from a commercial supplier such as, for example, the Sigma-Aldrich Corporation of St. Louis, Mo., USA. The system for performing high performance anion exchange chromatography and pulsed amperometric detection was purchased from Dionex Corporation of Sunnyvale, Calif., USA.

The results, which are shown in FIG. 3, were plotted using a computer software for statistical analysis and graphical presentation of data (JMP®, available from SAS Institute, Cary, N.C., USA). The highest levels of sialylation of TNFR: Fc were observed at 3 mM each fructose, galactose, and mannose and slightly over 5 mM N-acetylmannosamine. However, when 3 mM fructose, galactose, and mannose are added to cultures containing slightly less than 3 mM N-acetylmannosamine, levels of sialylation are almost equal to those seen using about 5 mM N-acetyl-mannosamine.

What is claimed is:

1. A method for increasing the sialic acid content of a protein produced by CHO cells comprising culturing the CHO cells in a medium comprising mannose, galactose, fructose, and N-acetylmannosamine, wherein culturing the CHO cells in the medium can increase the sialylation of a protein produced by the CHO cells.

2. The method of claim 1, wherein the medium is serum free.

3. The method of claim 1, wherein the CHO cells are cultured in the medium during a production phase.

4. The method of claim 1, wherein the concentrations of galactose, mannose, and fructose in the medium are each from about 1 mM to about 10 mM and the concentration of N-acetylmannosamine in the medium is at least about 0.8 mM.

5. The method of claim 1, wherein the concentrations of galactose, mannose, and fructose in the medium are each from about 1.5 mM to about 4.5 mM.

6. The method of claim 1, wherein the protein is a secreted, recombinant protein.

7. The method of claim 1, wherein the CHO cells are cultured at a temperature from about 29° C. to about 36° C.

8. A method for increasing the sialic acid content of a protein produced by CHO cells comprising culturing the CHO cells in a medium comprising galactose and N-acetylmannosamine, wherein culturing the CHO cells in the medium can increase the sialylation of a protein produced by the CHO cells.

9. The method of claim 8, wherein the medium is serum free.

10. The method of claim 8, wherein the CHO cells are cultured in the medium during a production phase.

11. The method of claim 8, wherein the concentration of galactose in the medium, is from about 1 mM to about 10 mM and the concentration of N-acetylmannosamine in the medium is at least about 0.8 mM.

12. The method of claim 8, wherein the concentration of galactose in the medium, is from about 1.5 mM to about 4.5 mM.

13. The method of claim 8, wherein the protein is a secreted, recombinant protein.

14. The method of claim 8, wherein the CHO cells are cultured at a temperature from about 29° C. to about 36° C.

15. A method for increasing the sialic acid content of a protein produced by CHO cells comprising culturing the CHO cells in a medium comprising mannose, fructose, and galactose, wherein culturing the CHO cells in the medium can increase the sialylation of a protein produced by the CHO cells.

16. The method of claim 15, wherein the medium is serum free.

17. The method of claim 15, wherein the CHO cells are cultured in the medium during a production phase.

18. The method of claim 15, wherein the concentrations of galactose, mannose, and fructose in the medium are each from about 1 mM to about 10 mM.

19. The method of claim 18, wherein the concentrations of galactose, mannose, and fructose in the medium are each from about 1.5 mM to about 4.5 mM.

20. The method of claim 15, wherein the protein is a secreted, recombinant protein.

21. The method of claim 15, wherein the CHO cells are cultured at a temperature from about 29° C. to about 36° C.

22. A method for increasing the sialic acid content of a protein produced by CHO cells comprising culturing the CHO cells in a medium comprising fructose and galactose, wherein culturing the CHO cells in the medium can increase the sialylation of a protein produced by the CHO cells.

23. The method of claim 22, wherein the medium is serum free.

24. The method of claim 22, wherein the CHO cells are cultured in the medium during a production phase.

25. The method of claim 22, wherein the concentrations of galactose and fructose in the medium are each from about 1 mM to about 10 mM.

26. The method of claim 25, wherein the concentrations of galactose and fructose in the medium are each from about 1.5 mM to about 4.5 mM.

27. The method of claim 22, wherein the protein is a secreted, recombinant protein.

28. The method of claim 22, wherein the CHO cells are cultured at a temperature from about 29° C. to about 36° C.

* * * * *